US007012096B2

(12) United States Patent
Dosch et al.

(10) Patent No.: US 7,012,096 B2
(45) Date of Patent: Mar. 14, 2006

(54) COMPOSITION FOR PAIN MEDIATION AND APPARATUS AND METHOD OF USE THEREOF

(75) Inventors: Michael H. Dosch, Toronto (CA); Xiaomao Li, Toronto (CA); Kurt Osterman, Scarborough (CA)

(73) Assignee: Palladin Healthcare International, Inc., Toronto (CA)

( * ) Notice: Subject to any disclaimer, the term of this patent is extended or adjusted under 35 U.S.C. 154(b) by 306 days.

(21) Appl. No.: 10/232,080

(22) Filed: Aug. 30, 2002

(65) Prior Publication Data

US 2003/0045576 A1     Mar. 6, 2003

Related U.S. Application Data

(60) Division of application No. 09/590,819, filed on Jun. 9, 2002, now Pat. No. 6,469,066, which is a continuation-in-part of application No. 09/215,235, filed on Dec. 18, 1998, now abandoned.

(51) Int. Cl.
| | |
|---|---|
| A61K 31/19 | (2006.01) |
| A61K 31/191 | (2006.01) |
| A61K 31/195 | (2006.01) |
| A61P 17/02 | (2006.01) |
| A61P 29/00 | (2006.01) |

(52) U.S. Cl. ............................. 514/557; 424/DIG. 13; 424/487; 514/566; 514/783

(58) Field of Classification Search ................ 514/557, 514/566, 783; 424/DIG. 13, 487
See application file for complete search history.

(56) References Cited

U.S. PATENT DOCUMENTS

| | | | |
|---|---|---|---|
| 2,338,416 | A | 1/1944 | Fales |
| 4,948,575 | A | 8/1990 | Cole et al. |
| 5,271,943 | A | 12/1993 | Bogart et al. |
| 5,362,488 | A | 11/1994 | Sibley et al. |
| 5,560,916 | A | 10/1996 | Koulbanis et al. |
| 5,616,619 | A | 4/1997 | Stofer |
| 5,674,912 | A | 10/1997 | Martin |
| 5,902,600 | A | 5/1999 | Woller et al. |
| 6,469,066 | B1 * | 10/2002 | Dosch et al. ............... 514/557 |

FOREIGN PATENT DOCUMENTS

WO     WO 98/26789     6/1998

* cited by examiner

*Primary Examiner*—Edward J. Webman
(74) *Attorney, Agent, or Firm*—McHale & Slavin, P.A.

(57) ABSTRACT

The present invention is directed to a composition for treating burns. The composition comprises a therapeutically effective amount of one or more weak organic acid compatible with human skin, in a pharmacologically effective carrier delivered at a pH of about 2.5–4.5. The weak organic acid is preferably selected from the group consisting of acetic acid, vinegar, citric acid and combinations thereof and the pharmacologically effective carrier is preferably an aqueous based carrier, more preferably a gel form, utilizing a CARBOPOL as a gelling agent. The composition may also include one or more other agents selected from sun blocking agents, skin moisturizing agents, herb extracts and antimicrobial agents.

25 Claims, 3 Drawing Sheets

| pilot test (log number) | Heat delivery (Probe) | Gel (active ingred.) | Strength | Pain relief (0-5) | Blister | Hyperalgesia | Infection | Scar |
|---|---|---|---|---|---|---|---|---|
| 1 | P | Vinegar | 4% | 5 | no | no | no | no |
| 2 | P | Vinegar | 4% | 5 | no | no | no | no |
| 3 | P | Vinegar | 5% | 5 | no | no | no | no |
| 4 | P | Vinegar | 5% | 5 | no | no | no | no |
| 5 | P | Vinegar | 5% | 5 | no | no | no | no |
| 6 | P | Vinegar | 6% | light burning interrupted | | | | |
| 7 | P | Vinegar | 6% | light burning interrupted | | | | |
| 8 | P | Vinegar | 5% | 5 | no | no | no | no |
| 9 | P | Citric Acid | 5% | 3 | no | no | no | no |
| 10 | P | Citric Acid | 5% | 4 | no | no | no | no |
| 11 | P | Citric Acid | 6% | 4 | no | no | no | no |
| 12 | P | Citric Acid | 6% | 4 | no | no | no | no |
| 13 | P | Citric + Acetic Acid/Vinegar | 4% + 1% | 4.5 | no | no | no | no |
| 14 | P | Citric + Acetic Acid/Vinegar | 4% + 1% | 4.5 | no | no | no | no |
| 15 | P | Citric + Acetic Acid/Vinegar | 4% + 1% | 4.5 | no | no | no | no |
| 16 | P | Citric + Acetic Acid/Vinegar | 5% + 1% | 5 | no | no | no | no |
| 17 | P | Citric + Acetic Acid/Vinegar | 5% + 1% | 5 | no | no | no | no |
| 18 | P | Citric + Acetic Acid/Vinegar | 5% + 1% | 5 | no | no | no | no |
| 19 | P | Citric + Acetic Acid/Vinegar | 5% + 1% | 5 | no | no | no | no |
| 20 | P | Citric + Acetic Acid/Vinegar | 5% + 2% | light burning interrupted | | | | |
| 21 | P | Citric + Acetic Acid/Vinegar | 5% + 2% | light burning interrupted | | | | |
| 22 | P | Na-Acetate | 5% | 0.5 | *yes | *yes | *no | *no |
| 23 | P | Na-Acetate | 5% | 0 | *yes | *yes | *no | *no |
| 24 | P | Na-Acetate | 5% | 0 | *yes | *yes | *no | *no |
| 25 | P | Acetic Acid (pure) | 5% | 4 | no | no | no | no |
| 26 | P | Acetic Acid (pure) | 5% | 4.5 | no | no | no | no |
| 27 | P | Acetic Acid (pure) | 5% | 4.5 | no | no | no | no |
| 28 | G | Vinegar | 5% | 5 | no | no | no | no |
| 29 | G | Vinegar | 5% | 5 | no | no | no | no |
| 30 | G | Vinegar | 5% | 5 | no | no | no | no |
| 31 | G | Vinegar | 5% | 5 | no | no | no | no |
| 32 | G | Citric Acid | 5% | 3 | no | no | no | no |
| 33 | G | Citric Acid | 5% | 5 | no | no | no | no |
| 34 | G | Citric Acid | 6% | 4 | no | no | no | no |
| 35 | G | Citric Acid | 6% | 4 | no | no | no | no |
| 36 | G | Citric + Acetic Acid/Vinegar | 4% + 1% | 4.5 | no | no | no | no |
| 37 | G | Citric + Acetic Acid/Vinegar | 4% + 1% | 5 | no | no | no | no |
| 38 | G | Citric + Acetic Acid/Vinegar | 4% + 1% | 4 | no | no | no | no |
| 39 | G | Citric + Acetic Acid/Vinegar | 5% + 1% | 5 | no | no | no | no |
| 40 | G | Citric + Acetic Acid/Vinegar | 5% + 1% | 5 | no | no | no | no |
| 41 | G | Citric + Acetic Acid/Vinegar | 5% + 1% | 5 | no | no | no | no |
| 42 | G | Citric + Acetic Acid/Vinegar | 5% + 1% | 5 | no | no | no | no |
| 43 | G | Na-Acetate | 5% | 1 | *yes | *yes | *no | *no |
| 44 | G | Na-Acetate | 5% | 0 | *yes | *yes | *no | *no |
| 45 | G | Na-Acetate | 5% | 0 | *yes | *yes | *no | *no |
| 46 | G | Acetic Acid (pure) | 5% | 4 | no | no | no | no |
| 47 | G | Acetic Acid (pure) | 5% | 5 | no | no | no | no |
| 48 | G | Acetic Acid (pure) | 5% | 4.5 | no | no | no | no |

* test gel removed after 60-120 minutes, 5% citric + 1% acetic acid gel applied

Figure 3

| Case # | Thermo - Trauma | Location | Initial Gel active ingredient | Pain (0-5) | Pain disappeared (minutes) | Blisters | Hyperalgesia |
|---|---|---|---|---|---|---|---|
| 13 | Hot Soup | dorsal hand | Vinegar (@ 5% acetic acid) | 4 | 0.15 | no | no |
| 14 | Fajita frying pan | dorsal hand | Vinegar (@ 5% acetic acid) | 5 | 0.15 | no | no |
| 15 | Hot Coffee | 3 Fingers | Vinegar (@ 5% acetic acid) | 4.5 | 0.1 | no | no |
| 16 | Fajita frying pan | Thumb | Vinegar (@ 5% acetic acid) | 5 | 0.15 | no | no |
| 17 | Roasting pan | ventral hand | Vinegar (@ 5% acetic acid) | 5 | 0.15 | no | no |
| 18 | Hot oil | dorsair hand | Vinegar (@ 5% acetic acid) | 4.5 | 0 | no | no |
| 19 | Hot plate | 3 Fingers | 5% acetic acid (pure) | 4 | 0.2 | no | no |
| 20 | Hot soup | dorso-ventral arm | 5% citric acid (pure) | 4.5 | 0.35 | no | no |
| 21 | Hot oil | dorsal hand | 5% Citric Acid &1% Vinegar | 4 | 0.1 | no | no |
| 22 | Frying pan | ventral forearm | 4% Citric Acid & 1% Vinegar | 4.5 | 0.2 | no | no |
| 23 | Frying pan | dorsal forearm | 5% Citric Acid & 1% acetic acid | 4.5 | 0 | no | no |
| 24 | Frying pan | upper arm | 5% Citric Acid & 1% vinegar | 4.5 | 0 | no | no |
| 25 | Glue Gun | dorsal forearm | none, gel only, pH 7.2 | 4 | *2 hours | yes | *no |

* vinegar gel applied after 2 hr, 4 times over 2 hr period

COMPOSITION FOR PAIN MEDIATION AND APPARATUS AND METHOD OF USE THEREOF

This application is a divisional of Ser. No. 09/590,819, filed Jun. 9, 2002, now U.S. Pat. No. 6,469,066, which is a continuation-in-part of Ser. No. 09/215,235, filed on Dec. 18, 1998 now abandoned, which has a priority date of Dec. 9, 1998 by reliance on Canadian application 2,255,521, the contents of all of said applications being herein incorporated by reference.

FIELD OF THE INVENTION

The present invention is directed to compositions useful for the treatment of burns, particularly compositions and their method and environment of use including a weak acid in a gel-like carrier evidencing a demonstrated efficacy in ameliorating the sensation of pain.

BACKGROUND OF THE INVENTION

Burns due to skin contact with flame, hot surfaces, hot liquids etc. are among the three most common accidents, both at the workplace and at home. The effective treatment of burn injuries continues to be a significant concern in the medical field. In North America, it is estimated that about 95% of all burn injuries are treated by home remedies, 2.5 million subjects seek medical advice for burns annually in the US., with about 100,000 of these requiring hospitalization [W. F., Am. Physician, :1321, 1992].

European figures are similar, with about 5% of burn injuries that come to medical attention admitted to hospital and a mortality rate of 0.2% [Jonsson Gynaecol :168, 1980; Hytonen Gynaecol : 218, 1987; de, Burns, :58, 1994]. Most of the burn injuries occur at home, and are essentially scalding accidents with gender and age distributions varying widely by region, urbanization and education. These figures do not include sunburn injury.

The psycho-social impact of burn injuries is dramatic. Over 95% of the costs are incurred by severe injuries, mostly (~two thirds) in terms of lost working days and to a lesser extent for direct care [de, Ann. Acad. Med. Singapore, :680, 1994; Hansbrough, J. Burn Care Rehabil :377, 1995]. There are, however, essentially no published data that analyze the epidemiology and impact of burn injuries which do not reach medical attention, but which often do cause loss of working days and considerable, if transient reductions in quality of life [Miller, . Physician, :167, 1977; Mertens . North Am., :343, 1997].

The main immediate burn injury problems include pain and primary infection. Scarring and functional impairment characterize the intermediate term. Malignancy represents a long term risk, although this is rare for most burns except those from ultraviolet and other radiation. Beyond the well known misery of burn pains, the objective threats, severity and prognosis of burn injuries are all functions of injury extent, i.e. surface area and depth of tissue destruction. The total tissue destruction is the sum of cells directly destroyed by heat and the much larger number of cells dying due to local tissue responses including edema, leukocytic infiltration, local mediators, apoptosis and primary infection. These elements are fundamental and similar in small as well as massive burn injuries, the latter adding systemic responses in a critical care scenario with mortality rates increasing as a quantitative function of tissue loss, infection and post-burn immunosuppression.

The principles of burn therapy have changed little over the past decades, and there is some lack of basic science and animal models for in depth analysis of the cellular and molecular events following tissue burn injury. There is long-standing consensus for rapid and aggressive intervention following burn injury, including the early use of skin grafting. One conclusion from this recognized need for rapid intervention is that following the direct tissue destruction by the hyperthermal insult, it is local and systemic biological responses that determine much of the post-injury course.

This scenario is analogous to, and may include, the development of shock syndromes which can be by themselves life threatening, independently of the nature and extent of a given injury [Cason, Pediatr . Surg.,:3, 1981]. Other than shock, however, the immediate interference with tissue injury responses following thermotrauma has received little attention beyond general pain relief and precaution against infection [Baxter, C. R. and Waeckerle :1305, 1988; Brofeldt, J. Burn Care Rehabil., :63, 1989]. Secondary cell death due to tissue burn injury responses involves the elements of acute phase reactants such as leukocyte extravasation and mediator release. Vasoconstriction occurs peripheral to the injury locus but hyperemia and fluid loss within the injured area conspire to reduce oxygenation, accumulate toxic detritus, and activate complement and apoptosis pathways for pronounced secondary cell death. These events create the vicious circle characteristic of even small burn injuries and their misery [Shaw, A, Br. J. Hosp. Med., :583, 1994; Arturson, G., Burns,: 255, 1996].

In addition, the injured tissue represents an ideal, immunologically underprivileged target site for infectious agents which can dramatically threaten the recovery process. While the need to cover burn injuries has long been recognized, ideal solutions are still elusive, and the variety of proposed remedies is profuse, ranging from honey, tree bark and animal urine or dung to potato peels to amniotic membranes, allografts and modern plastics to name but a few.

The use of tannic acids (TA) (or tannic herb extracts) as a burn remedy had been proposed early this century [Davidson, E. C., Surg. Gynecol. Obstet., 1925] based upon ancient Chinese texts. TA is the collective name for a group of undefined substances which convert putrefiable hide or skin into imputrescible leather. TA occurs in most parts of the vegetable kingdom and is more prevalent among the higher plants, especially in the barks of trees (cited from: Hupkens, Burns,:57, 1995). The acidity of these extracts is uncertain, as hydroxy groups from the trihydroxybenzene structure are extremely weak proton donors. The often ill described tannic herb extracts differed in their hepatotoxicity and tendency towards secondary infection [Hupkens, 1995]. TA treatment has been linked to liver necrosis in burn patients and even death: in one report 14 of 16 TA-treated patients who died from their burn trauma showed definitive evidence of serious liver necrosis (reviewed in [Hupkens, 1995]). This level of toxicity is unacceptable and has lead to the disappearance of TA from medical practice, although the burn toxins (a 70 year old concept no longer acceptable) released in the wound and relied on TAs ability to absorb/precipitate these putative toxins.

The use of vinegar as an antimicrobial agent is as old as the use of alcohol, and by around 1000 AD, hand washing with vinegar was recommended in ancient medical texts from China and Arabic sources such as (1031–1095 AD) [Chan, Nephrol: 295, 1994].

Vinegar is an impure organic acid and a rich source of many volatile contaminants [De, Food Add. Contam 161, 1987]. It has possible antibacterial and antiviral effects, although the mechanisms of this vinegar activity is unknown. Vinegar is approved for human non-dietary use and performs well as the main ingredient of vaginal douches although mechanisms are, again, uncertain [Brinton Gynecol :49, 1990; Nyirjesy, Obstet. Gynecol :50, 1997]. The effectiveness of pure acetic acid, sodium acetate and vinegar have rarely been compared [Brighenti:242, 1995], and never with respect to antimicrobial activity. Although sodium acetate is used in some vaginal douches, their effectiveness has not been measured [Chvapil, Obstet. Gynecol :88, 1978]. While acid sensitivity of bacteria is one element of antimicrobial activity, this is insufficient to explain the antimicrobial effects of vinegar, since some common food-borne bacteria are highly sensitive to vinegar, yet they survive gastric acid exposure and cause common intestinal disease [Nishikawa, Int. J. Food Microbiol., :271, 1993]. There is a considerable amount of published literature on the antimicrobial effects of vinegar [Larghi. Argent. Microbiol :86, 1975; Fasanella, Ophthalmic. Surg., 1991; Karapinar, S. A., Int. J. Food Microbiol :261, 1992; Nishikawa Ostomy. Wound Manage., :18, 1996], observations that are finding their way into the food processing industries [Dickens :576, 1994; Entani Kansenshogaku Zasshi :443, 1997]. While vinegar treatment of killed chicken prior to freezing was shown to significantly reduce bacterial contamination, there are no published reports on the effects of vinegar on living skin [Dickens, 1994]. A widely employed skin application of vinegar occurs in the Pacific Rim Countries where, acting as a nematocyst inhibitor, vinegar is the recommended first aid treatment against potentially life threatening jelly fish stings [Fenner, Med. J. Aust., :550, 1985; Beadnell Med. J. Aust., :655, 1992; Fenner, Med. J. Aust., :498, 1993]. In vitro tissue culture studies suggested that acetic acid is toxic to human fibroblasts and keratinocytes in concentrations of above 0.025% (reviewed in [, C. R., 1996]). These data contrast with the frequent use of vinegar douches, which are tolerated well and over prolonged periods of intravaginal use [Nyirjesy, Obstet. Gynecol:50, 1997].

DESCRIPTION OF THE PRIOR ART

U.S. Pat. No. 5,902,600 discloses a wound dressing of glycerin polyacrylate gel.

U.S. Pat. No. 5,674,912 relates to a sunscreen and wound healing composition of pyruvic acid and various fatty acids.

U.S. Pat. No. 5,616,619 provides a burn treatment paste containing salt and lemon juice.

U.S. Pat. No. 5,560,916 is illustrative of an anti-aging dermatological composition of vinegar in a gel matrix.

U.S. Pat. No. 5,362,488 teaches a buffered skin or diaper rash cream containing a silicone polymer including citrate, citric acid and additional ingredients.

U.S. Pat. No. 5,271,943 is drawn to a wound treatment gel of salt and guar or locust gum.

U.S. Pat. No. 4,948,575 describes an alginate hydrogel foam with acetic acid and metal salts.

U.S. Pat. No. 2,338,416 describes a sunburn preparation containing aloin, agar, benzoic acid and glycerin.

The prior art fails to disclose a composition and method for its step-wise production wherein particular gelling agents, in combination with specific amounts of a pain reducing effective amount of a weak acid, e.g. acetic acid, citric acid or a combination thereof, and optionally in the presence of EDTA, are manufactured in accordance with particular production parameters which result in a particularly efficacious pain reducing dressing.

SUMMARY OF THE INVENTION

The present invention provides a composition containing a weak acid blended according to particular process parameters within a gel-like carrier. The gel may be used alone, e.g. in its gelled form or in the form of a spray. It is also within the scope of the instant invention to form various articles which demonstrate the efficacious properties of the gel composition manifested in the form of a wound dressing, an absorbent bandage, a feminine hygiene product, a diaper, or the like.

Accordingly, it is a primary objective of the present invention to provide compositions for the treatment of skin injuries, primarily burns or similar burn-like irritations.

It is a further objective of the present invention to provide a composition for treating burns comprising a therapeutically effective amount of one or more weak organic acids.

It is yet another objective of the invention to select the therapeutically effective organic acids from a group including, but not limited to, acetic acid, vinegar, citric acid or combinations thereof, in a pharmacologically effective carrier, wherein the pH of the composition ranges from about 2.5 to 4.5.

It is still an additional objective of the instant invention to provide a kit for the treatment of burns comprising:

a composition for treating burns comprising a therapeutically effective amount of one or more weak organic acids as defined supra, said acids being incorporated within a pharmacologically effective carrier, and wherein the pH of the composition ranges from about 2.5 to 4.5;

wrapping or bandage materials; and instructions for use.

It is yet another objective of the invention to provide a pharmacologically effective carrier for the acid which is in the form of an aqueous based carrier, preferably a gel form, utilizing a CARBOPOL gelling agent or equivalent.

It is a still further embodiment of the invention to include one or more additional agents, incorporated within the acid containing gel matrix, said agents including, but not limited to sun blocking agents, skin moisturizing agents, herb extracts and antimicrobial agents.

It is a still further objective of the invention to teach a method for treating skin trauma arising from sources including, but not limited to thermal, chemical, light sources, or the like wherein the method includes application to the affected area of the skin of a therapeutically effective amount of an acid containing gel as described supra, wherein the pH ranges from about 2.5 to 4.5, preferably between 4.1 and 4.4, most preferably 4.15 to 4.25, and optimally at 4.2.

It is still an additional objective of the instant invention to provide a form of skin treatment effective to provide sustained localized concentrations of H+ ions.

It is a further objective of the instant invention to mediate the perception of pain by providing effective intervention within the nociceptor pathways.

It is still another objective of the instant invention to provide a composition and process for promoting scar-less wound healing.

Other objects and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

BRIEF DESCRIPTION OF THE FIGURES

FIG. 2 presents data obtained from the treatment of 48 non-accidental burn wounds treated with various compositions;

DETAILED DESCRIPTION OF THE INVENTION

For the purpose of better understanding the invention, the term, burn, means an area of tissue damage, caused by excessive exposure to thermal, frictional, chemical, electrical, radiation and/or radioactive agents. The effects may be local, resulting in cell injury or death, or both local and systemic. Burns are classified according to the depth of the tissue damage.

The present invention is directed to a composition for treating burns where the composition is effective to provide immediate interference with the tissue injury responses following trauma. In contrast to topical local analgesics, which do not affect aspects of wound healing, local or systemic responses [Pedersen, J. L., 1996], the compositions of the present invention provide both, analgesia and distinct effects on the tissue injury response which is reflected in the beneficial course of scar-less healing.

The present invention relies on the observed effectiveness of weak organic acids compatible with human skin as a burn therapeutic agent. The effectiveness of compositions of the invention has been shown using, for example, food-grade vinegar, diluted acetic acid or citric acid. Local delivery of the composition of the invention demonstrated a range of unexpected properties beneficial for the treatment of full and partial skin thickness thermal injuries due to flame, hot surface contact, scalding, as well as skin surface damage due to frictional trauma and overexposure to sunlight.

The application of the composition of this invention is counter-intuitive, as acids can cause burns themselves when encountered in sufficient concentration. Sources of concentrated acids can cause topical burns and should, thus, be avoided. In contrast, the present invention has established that an appropriate composition containing a weak acid, illustrated but not limited to, acetic acid, vinegar and citric acid, is effective for burn therapy. These concentration/dilutions are similar to the acetic acid content of food-grade vinegar and the citric acid content of natural lemon juice, respectively.

While not wishing to be bound to any particular mode of operation, it is theorized that the compositions of the instant invention target the initial oscillations of the cycle leading to secondary cell death, thereby preventing secondary cell death with consequent improvement of the post-injury healing process. This is evidenced by observations which point out that although the positive impact on localized burns is dramatic, reproducible and fast-acting, the beneficial effects nevertheless last beyond the 1–2 hrs of initial application.

As discussed above, the compositions of the present invention appear to stop the collateral damage due to the cascade of local responses to thermal insult. Without the pain and consequent vasoconstriction, without extravasation and consequent edema, infiltration, mediator release, inflammation and blister formation, the healing process can and does begin unimpeded. It is possible that the controversial antimicrobial effects of vinegar contribute to the remedial effects afforded by sub-neutral pH gels by reducing the local load of infectious agents and thus the risk for primary colonization [Emili, H et al., 1974; Larghi, O P et al., 1975; Fasanella, R M, 1991; Karapinar, M and Gonul, S A, 1992; Nishikawa, Y et al., 1993; Rund, C R, 1996; Entani, E et al., 1997]. However, infection is not a significant problem in the typical household burn addressed as the initial and tested target of this invention.

Formulations according to the present invention have demonstrated efficacy treating a variety of accidental and planned partial skin thickness first and second degree, as well as a number of small area third degree burns. In addition, the compositions of the invention have shown effectiveness in the treatment of sunburns in adult volunteers. In a blind study, test subjects were treated consecutively with different gel formulations that did or did not contain the active ingredient and were otherwise indistinguishable. These experiments firmly established the effectiveness of compositions of the invention.

Specifically, the effects of the compositions of the present invention include rapid local analgesia without the numbing of local anesthetics; prevention/rapid reduction of hyperemia; prevention or reduction of local edema; prevention of blister formation; prevention of wound infection; acceleration of wound healing; prevention of depigmentation; prevention of delayed hyperalgesia; and an absence of scarring and keloid formation and generalized elimination and/or reduction of inflammatory response.

While the majority of these effects are newly discovered and disclosed herein, it is noted that a possible antibacterial effect of vinegar and other apolar weak acids is controversial in the literature and, if present, could conceivably contribute to the excellent wound healing characteristics observed following early, transient application of the invention on surface burn injuries.

The compositions of the invention contain a carefully controlled acid concentration, typically derived from a weak organic acid compatible with human skin, preferably, an organic acid selected from acetic acid, vinegar, citric acid or combinations thereof. In a preferred embodiment, the composition comprises acetic acid or vinegar in an amount to yield up to about 0.5 to 5% acetic acid, and 2 to 8% citric acid. In a most preferred embodiment, the composition comprises acetic acid or vinegar in an amount equal to up to about 1% acetic acid and 5% citric acid.

The composition has a pH in the range of about 2.5 to about 4.5. The selection of the pH for the composition is dependent upon the formulation used and the ability of the other components in the formulation to tolerate the acidic pH. Preferably, the pH range for effectiveness is generally about 4.0 to about 4.5, with a preferred pH ranging from 4.1 to 4.4, a more preferred pH ranging from 4.15 to 4.25 and a most preferred pH of approximately 4.2. The gel formulations based upon CARBOPOL preferably have a pH of about 4.2 which aids in the formulation of the gel.

The composition is provided in a form suitable for the immediate application to the burn area. The composition may be in the form of a liquid, gel, lotion, aerosol, or may be provided in the form of a dressing for application to the skin. If desired, other water soluble agents such as herb extracts useful for soothing and cosmetic effects may be added provided they do not deleteriously affect the therapeutic properties of the composition.

The composition is formulated as a gel or lotion to provide for longer lasting coverage of the affected areas of the skin. The gel or lotion may be a water based gel using a suitable gelling or thickening agent. Alternatively the lotion may be provided as an emulsion, either an oil in water emulsion or a water in oil emulsion. Such emulsions typically are prepared using conventional ingredients including stiffeners, emollients, emulsifying agents and humectants. Stiffeners are usually oil-soluble fatty alcohols such as stearyl alcohol, cetyl alcohol, lauryl alcohol and myristyl alcohol. Emollients are usually isopropyl myristate, lanolin, lanolin derivatives, isopropyl palmitate, isopropyl stearate and the corresponding sebacates. Emulsifying agents are preferably non-ionic and are usually sorbitan monooleate and polyoxyl 40 stearate. humectants are usually propylene glycol, sorbitol, glycerin and mixtures thereof. The ingredients for the emulsion are selected to be compatible at the desired pH range of about 2.5 to about 4.5. A typical formulation is characterized according to the following where percentages are by weight:

| Component | % by weight |
|---|---|
| Petrolatum | 0–25 |
| Stiffener | 7–45 |
| Emollient | 0–15 |
| Emulsifying agent | 4–16 |
| Humectant | 7–40 |
| Weak Organic acid | 5 |
| Water q.s. | 100 |

The compositions of the present invention are preferably formulated as a water soluble gel which provides sustained concentrations of weak acid. The gel formulation, for example, can utilize CARBOPOL as the gelling agent. CARBOPOL is a common gelling agent in foods, cosmetics, prescription and OTC drugs, is highly hydrophilic and rapidly removed under running water. This allows for ease of re-application to prolong the analgesic effects of the composition. CARBOPOL polymers are available from the B. F. Goodrich Co. and are high molecular weight, crosslinked, acrylic acid-based polymers. CARBOPOL homopolymers are polymers of acrylic acid crosslinked with allyl sucrose or allylpentaerythritol. CARBOPOL copolymers are polymers of acrylic acid, modified by long chain (C10–C30) alkyl acrylates, and crosslinked with allylpentaerythritol. The resins are generally available as fluffy, white, dry powders (100% effective). The carboxyl groups provided by the acrylic acid backbone of the polymer are responsible for many of the product benefits. CARBOPOL resins have an average equivalent weight of 76 per carboxyl group.
Appearance: fluffy, white, mildly acidic powder
Bulk density: approximately 208 kg/m 3 (13 lbs ft 3)[1]
Specific gravity: 1.41
Moisture content as shipped: 2.0% maximum
Equilibrium moisture content: 8–10% (at 50% relative humidity)
$pK_a$: 6.0±0.5
pH of 1.0% water dispersion: 2.5–3.0
pH of 0.5% water dispersion: 2.7–3.5
Equivalent weight: 76±4
Ash content: 0.009 ppm (average)[2]
Glass transition temperature: 100–105°C. (212–221°F.)
  Polymers produced in cosolvent (a cyclohexane/ethyl acetate mixture) have a bulk density of 176 kg/m$^3$ (11 lbs/ft$^3$). Polymers produced in ethyl acetate have an ash content (as potassium sulfate) of 1–3% on average.
It will be apparent to those skilled in the art that other known gelling agents may be utilized in addition to or in place of CARBOPOL, provided they are effective to form a gel in the desired pH range and do not affect the usefulness of the organic acid.

The composition may also include herb extracts deemed attractive for their purported soothing and cosmetic effects. For example, a calibrated extract of Marigold and Aloe vera may improve odor and provide added soothing properties. Herb extractions can be performed as short term (20 min, 2.5° C.) vinegar or 5% acetic acid infusions of dried, powdered herbs at pH 2.7–0.3 (adjusted to approximately pH 4.2).

The compositions of the present invention may also be provided as an aerosol, preferably in a pump container to provide a suitable mist spray for application to the affected area. Such aerosol may be simply an aqueous solution of the weak organic acid or may include other ingredients typically provided in aerosols such as stiffeners, humectants, or herb extracts such as aloe vera so long as the additional ingredients do not affect the usefulness of the composition for burn therapy. An advantage of the aerosol form is that it can be applied to the affected area of the skin without requiring direct physical contact with the skin.

The compositions of the present invention may also be provided in the form of a dressing for application to the skin. The dressing can be a gauze, or other suitable sorbent material which is saturated with the composition of the present invention. The use of the dressing provides a physical barrier aiding in protection of the affected area from potentially abrading contact and exposure to microbial infection. This may aid in the healing of the affected area, especially for more severe burns. The use of a sorbent material, e.g. a sorbent fibrous matrix further provides a localized concentration of H+ in contact with the affected area for a prolonged period.

The compositions of the present invention may also be applied in the form of an absorbed gel which is maintained within the fibrous matrix of a sorbent article, e.g. a feminine hygiene product such as a pad or tampon, or alternatively a sorbent diaper or the like. While not wishing to be bound to a particular theory of operation, it is believed that as moisture is sorbed from the body, a pathway is provided for communication of the effective ingredients of the inventive composition with the associated dermal areas of contact.

The compositions of the present invention are of particular utility for small household and kitchen burns as well as sunburns, i.e. over 95% of burn/scald accidents in North America.

Delivery of the composition of the present invention as quickly as possible after the injury is an important element for its full effectiveness. Delayed application of the formulation shows slowly lessening effectiveness, but repeated administration hours after the insult has been tested successfully after sunburns to reduce pain, hyperemia and blister formation, and produce relief from thermal hypersensitivity.

Depending on wound depth and area, single or repeated acute application of the compositions of the invention leads to a high degree of functional recovery within minutes and excellent wound healing course without blistering and scarring even in subjects that tend to develop keloid. In subjects tested on one or more occasions to date, the composition of the invention has prevented development of depigmentation and delayed hyperalgesia.

While for most small burns, a single application of the composition of the invention provides effective relief, for optimum healing it is preferred that the composition be applied 2–4 times over the first two hours after the burn trauma.

The present invention has demonstrated, for the first time, that topical application of H+ (hydrogen ion) through an acidic formulation eliminates or, at least, significantly reduces the normal symptoms (hyperesthesia, blistering, etc.) and subsequent complications (infection, scarring, etc.) of first, second and small area third degree thermal injuries. The application also accelerates the healing process. While not wishing to be bound to a specific mode of operation, the cellular and molecular mechanisms of H+-based burn treatments appear to mediate the perception of pain by providing effective intervention within the nociceptor pathways. This realization provides a novel strategic method for burn therapy. The application of localized concentrations of H+ appears to provide a critical experimental tool in the study of nociceptor pathways, an area of research that has particular relevance in pain research—from burns and otherwise.

In order to prolong the beneficial effect of the composition within the burned area of local thermal injury, the composition is preferably provided as a gel formulation, for example using CARBOPOL 940 NF, a commercially available, commonly used thickening agent in food, cosmetic and various health care products. In addition, since herbs and/or their extracts have been traditionally used for their soothing effects, Aloe Vera, Marigold, their extracts and similar substances may be utilized in the acid gel. However, the possible effects or effectiveness of the latter is independent of and cannot affect the activities of the weak acid.

The embodiments of this invention may be formulated and provided in a kit format, comprising a composition for treating burns comprising a therapeutically effective amount of one or more weak organic acids selected from the group including acetic acid, vinegar, citric acid or combinations thereof in a pharmacologically effective carrier, wherein the pH of the composition ranges from 2.5 to 4.5, packaged along with wrapping, bandage, or sorbent personal care/hygiene materials or the like, and instructions for their use.

It is within the purview of the instant invention to include within said kit, additional substances that assist in occluding the damaged tissue from the environment, along with other substances that assist in the treatment of the burned skin. Applicators that assist in delivering the composition to damaged tissue may also be included in the kit.

Preferred embodiments of the invention will now be described in the following examples. It is to be appreciated that the invention is not limited to the specific examples which are merely illustrative of the preferred embodiments.

Preparation of Acid Gels

A. Two gels containing the following acids will be made:
1: 1% acetic acid (AA)/5% citric acid (CA) gel (200 mL)
2: 1% acetic acid/4% citric acid gel (200 mL)
No Herb Extract used.

B. Make the following solutions according to the above acid concentration specification containing 0.1% EDTA

|  | 5% CA + 1% AA | 4% CA + 1% AA |
|---|---|---|
| CA monohydrate (FW.210) | 11.0 g | 8.75 g |
| EDTA 120 g | 0.20 g | 0.20 g |
| Distilled Water | to 160 mL | to 160 mL |
| Vinegar (~5% acetic acid) | 40 mL | 40 mL |

C. Gel productions in ~300 ml beakers

Magnetic Stirring at Highest Setting (2500 rpm)

Very slowly add 3.6 g CARBOPOL 940 NF (1.8 g/100 ml) to the each of the above solutions through a fine metal mesh, avoiding clumps.

Stir until suspension is smooth and without white CARBOPOL flakes; if a few flakes remain, disperse with a spatula.

Add 10N NaOH 1 ml/0.5 ml/0.2 ml at a time to obtain pH 4.2 5% CA+1% AA: 10.3 mL of 10 N NaOH (5.2 mL NaOH/100 mL gel) 4% CA+1% AA: 9.0 mL of 10 N NaOH (4.5 mL NaOH/100 mL gel); gelling of CARBOPOL will soon stop magnetic stirrer action, remaining stirring is accomplished with spatula.

Transfer gel to 15 mL. and 50 mL. Falcon tubes and spin—5 min/2000 rpm (550 g) to degas the gel.

To avoid evaporation of acetic acid from vinegar it is important not to use vacuum to degas the mixture.

Other Gel Formulations:

Acetic acid and citric acid were each made to 5% (wt/v) in distilled H2O from glacial acetic acid (99.8%) and solid citric acid monohydrate (analytical grade), respectively. Mixtures comprising 4 or 5% citric acid and 1% acetic acid were also made from citric acid monohydrate and commercial, food-grade vinegar containing 5% acetic acid. Powdered dry marigold and Aloe Vera were then added to these acid solutions or to vinegar to 0.15% and 0.075%, respectively. This step is optional and omission of the herbs does not affect the potency of the final products. The mixtures were incubated and stirred at room temperature for 20 min, and cellulose filtered, followed by the addition of EDTA to 0.1%. Subsequently, solid CARBOPOL 940 NF or 980 NF was applied slowly to 1.8% while being stirred at high magnetic setting until the suspension lost granularity. 10N NaOH was then slowly stirred in to adjust pH of the mixtures to 4.2 for their gelling. For examples, for every 100 mL of the vinegar and 5% acetic acid gels, 2.8 mL of the alkaline solution was required, whereas for the 5% citric acid gel, 4.3 mL was required.

The actual requirement for 10N NaOH may vary slightly, depending on the specific pH parameter of the distilled water used. Finally, excess air was removed from the gel suspensions by low speed (2000 rpm) centrifugation at room temperature for 5 min.

As a control to the acid gels, a neutral (pH 7.0) gel was similarly made from distilled H2O, EDTA and CARBOPOL 940 NF or 980 NF. Since CARBOPOL mediated gelling is much more efficient at near neutral pH, significantly less CARBOPOL was used for the neutral gel. In addition, a neutral gel was also made from 5% acetic acid titrated with 10N NaOH.

These formulations are summarized below:

Preparation I: Vinegar Formulation

| Ingredient | Amount |
|---|---|
| Vinegar | 100 mL |
| EDTA | 0.1 g |
| CARBOPOL | 1.8 g |
| 10N NaOH | 2.8 mL |

Preparation II: 5% Acetic Acid Formulation

| Ingredient | Amount |
| --- | --- |
| glacial acetic acid (99.8%) | 5.01 mL |
| Distilled H$_2$O | 94.99 mL |
| EDTA | 0.1 g |
| CARBOPOL | 1.8 g |
| 10N NaOH | 2.8 mL |

Preparation III: 5% Citric Acid Formulation

| Ingredient | Amount |
| --- | --- |
| Citric acid monohydrate | 5.5 g |
| Distilled H$_2$O | to 100 mL |
| EDTA | 0.1 g |
| CARBOPOL | 1.8 g |
| 10N NaOH | 4.3 mL |

Preparation IV: 5% Citric Acid+Vinegar Formulation

| Ingredient | Amount |
| --- | --- |
| Citric acid monohydrate | 5.5 g |
| Distilled H$_2$O | to 80 mL |
| Vinegar | 20 mL |
| EDTA | 0.1 g |
| CARBOPOL | 1.8 g |
| 10N NaOH | 5.2 mL |

Preparation V: 4% Citric Acid+Vinegar Formulation

| Ingredient | Amount |
| --- | --- |
| Citric acid monohydrate | 4.4 g |
| Distilled H$_2$O | to 80 mL |
| Vinegar | 20 mL |
| EDTA | 0.1 g |
| CARBOPOL | 1.8 g |
| 10N NaOH | 4.5 mL |

Preparation VI: Distilled H$_2$O Formulation at pH 7.0

| Ingredient | Amount |
| --- | --- |
| Distilled H$_2$O | 600 mL |
| EDTA | 0.1 g |
| CARBOPOL | 1.8 g |
| 10N NaOH | 1.9 mL |

Preparation VII: Neutral Formulation (pH 7.0) from 5% Acetic Acid and NaOH

| Ingredient | Amount |
| --- | --- |
| glacial acetic acid (99.8%) | 5.01 mL |
| Distilled H$_2$O | 94.99 mL |
| EDTA | 0.1 g |
| CARBOPOL | 1.8 g |
| 10N NaOH | 11.0 mL |

Application of the active ingredients in a clean gel form is particularly preferred as it adds benefits intrinsic to a controlled, tested and quality assured product. In particular, a gel provides sustained delivery of active ingredient(s) for a reasonable time as well as a shield from microbial attack. A gel formulation and packaging in UV resistant containers reduces loss of volatiles [De, V M et al., 1987] and allows addition of ingredients to augment its healing properties, smell, cosmetic appeal, transportability and shelf life.

The effectiveness of the burn therapy of the present invention is enhanced by quick application, preferably right after the thermal insult. A period of less than 5 minutes between insult and application is optimal, 10–30 minutes is acceptable. The effectiveness is further enhanced by 2 to 4 repeat applications over the first 1 to 2 hours, especially for relief of pain associated with the thermal injury. Beyond that time frame, further applications of the compositions generally do not provide enhanced therapeutic effect. In sunburns where burn trauma is acquired over a prolonged period of time, the effect of the composition is less immediate, and in severe cases may require repeated applications over the first several hours of treatment.

The compositions of the invention are applied liberally over the affected skin area directly and quickly. Positive results are essentially immediate. The pain relief is dramatic, quick and lasting after single or repeated application within the first 2 hours of trauma. If not complete, the composition of the invention can be freely re-applied. This is especially true for the gel which rinses off instantly with water if required.

The immediate perception following application of the composition of the invention is a cooling, soothing effect, followed by receding wound pain. It has been typical that burn victims will pursue whatever activity preceded the accident within some 5–10 minutes and essentially forget the insult. In superficial burns the typical post-burn hyperalgesia disappears within 10–15 minutes, in deeper injuries this process takes a day, but does not impede the ability to have, for example, a normal shower, re-applying if subjective or objective symptoms (edema, hyperemia) linger, as was the case with several small, but full thickness skin thermo-traumas successfully treated with the composition of the invention. The absence of scarring has been observed with all test applications (including the above third degree burns), as has the absence of blistering. This applies as well to superficial, intermediate and deep partial skin thickness burns.

Initial impressions pointed to occasional depigmentation [Kahn, A M and Cohen, M J, 1996], until it became clear that affected skin areas had light to absent pigmentation that contrasted with the tanned surrounding. These lighter areas later tanned in concert with their surrounding skin without demarcation. This observation indicates effective replacement of the injured skin area with healthy new skin tissue rather then collagen-rich, melanocyte depleted scar tissue.

Scar formation is a serious difficulty in burn management, yet the understanding of functional tissue elements and tissue injury responses that drive scar development are in their infancy [Swann, D A et al., 1988; Carr, C J, 1992; Robson, M C et al., 1992; Garg, H G et al., 1993; Gibbons, M et al., 1994; Garg, H G et al., 1995; Ghahary, A et al., 1995; Harland, D L et al., 1997]. Analyses of the mechanisms that prevent scar formation following treatment with the composition of the invention may shed new light and delineate possible new therapeutic strategies in this central area of burn management.

The effectiveness of the composition of the invention in cases of sunburn, including one serious case with burn to some 40% of body surface area has been demonstrated. In sunburns the thermal and radiation injury accumulates relatively slowly and evenly over the affected areas. The composition of the invention was applied within one hour after leaving the sun, i.e. much later in the burn response process than after acute heat burns. The effect of the composition of the invention was dramatic, but much slower. The impressive hyperemia receded within an hour of freely applying and re-applying the composition of the invention, interestingly leaving out several small areas unintentionally not covered by the gel. Pain was felt in these areas. This implies strictly local mechanisms of action. By the end of the day, this victim had a lukewarm shower to remove some dry gel residue—the gel dissolves instantly in water—and a thin layer was applied for the night, including areas previously uncovered but still showing local hyperalgesia and hyperemia. There was no sign of sunburn next day, the skin was comfortable to touch. The skin showed no hypersensitivity to re-exposure to sun. However, sunblocks were used more freely. There was development of natural tan, suggesting restoration of normal skin response to sunlight.

Figure 1:
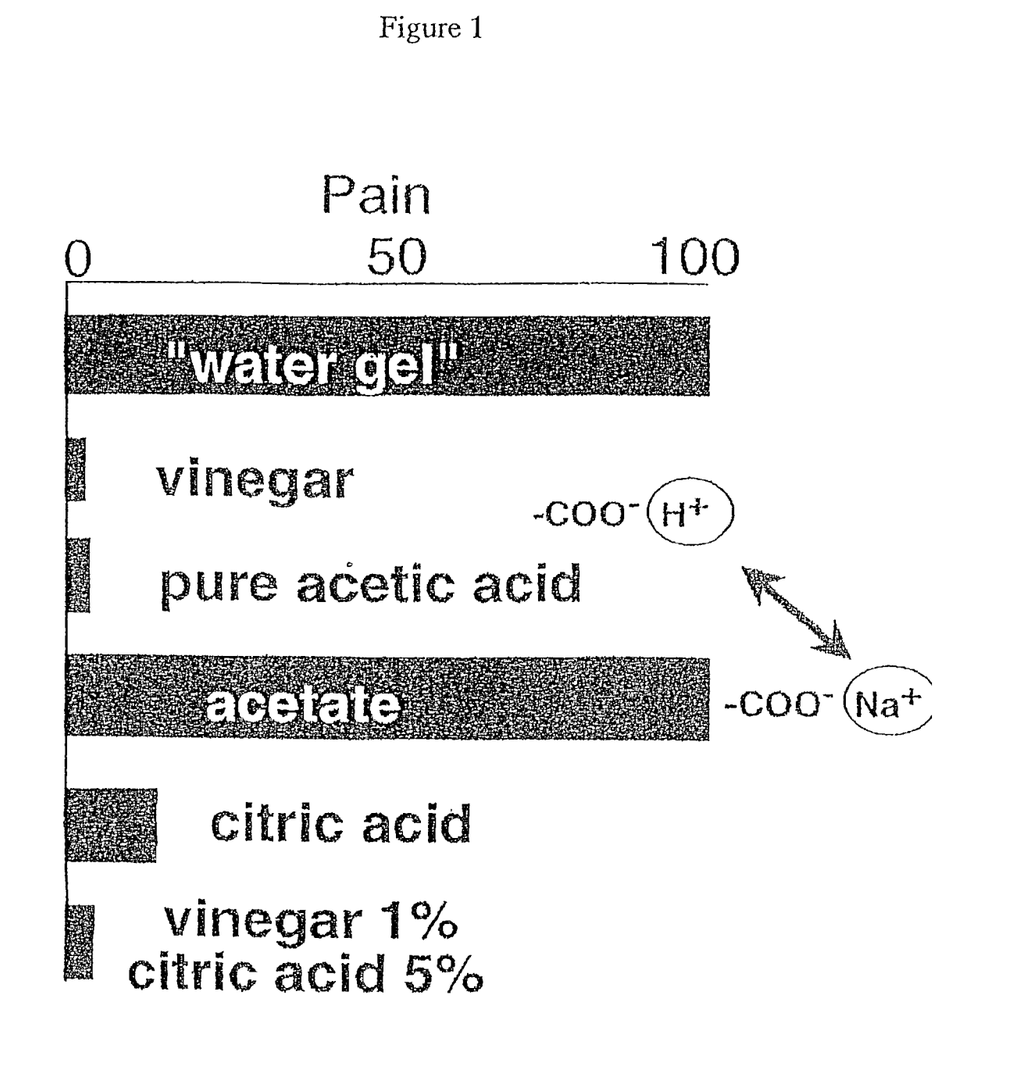
FIG. 1 illustrates data relating to patient's perception of pain, after treatment of burns with various compositions.

FIG. 1 illustrates data relating to patient's perception of pain, after treatment of burns with various compositions.

EXAMPLES

Example 1

In vivo Testing of the Acid Gel in Subjects with Thermal Skin Injury

Forty seven adult volunteers were recruited into these studies. These subjects had undergone accidental or voluntary partial skin thickness surface burns. They were treated with the compositions prepared as above at pH 4.2, or aqueous solutions of 5% acetic acid at pH 2.7. Some of the test subjects underwent testing on repeated occasions. This included the two near-full thickness (third degree) small area burns tested: both were successfully treated. The main measured response elements were: speed and extent of local analgesia, development and extent of hyperemia, development and extent of local edema, development and extent of blister formation, development and extent of wound infection, time course of wound healing, development and extent of depigmentation; development and extent of delayed hyperalgesia; development and extent of scarring and keloid formation.

The initial formulations were vinegar-based, but subsequently formulations based on typically 5% acetic or citric acid were developed and compared to neutral pH (water-based) control gels. All formulations with weak acid of the invention performed in a similar fashion, employing a blinded subsequence (N-of-one) protocol.

The application of a liquid composition was reasonably effective to provide pain relief. It is preferred that the composition is provided in a carrier medium to maintain the contact of the composition with the skin for extended periods. Such carrier medium may be either a physical object such as sponge, gauze, tissue or towel to contain the liquid in the place of injury or may be a more viscous composition such as a gel or lotion. The results of these experiments are summarized in FIG. 2.

Figure 3:
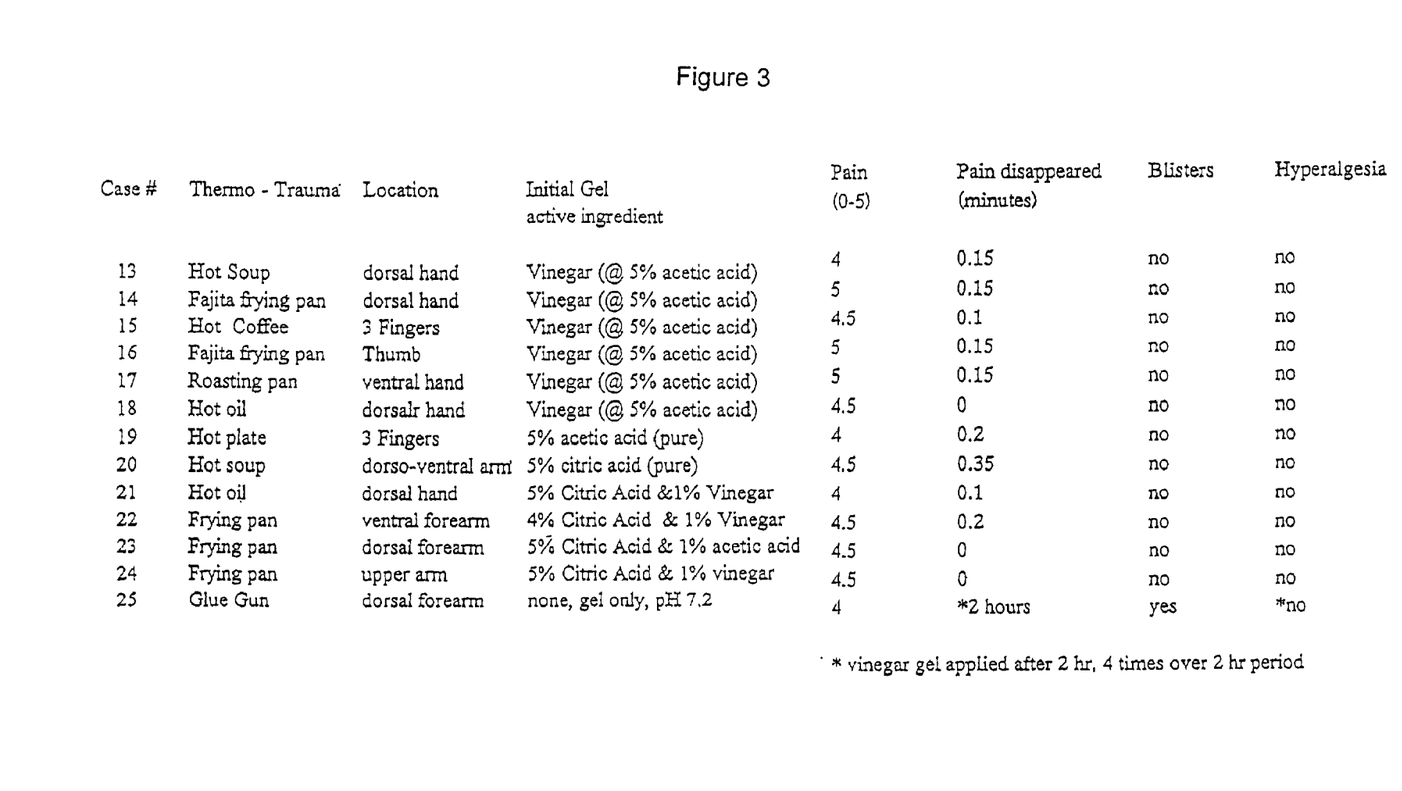
FIG. 3 presents data obtained from the treatment of 13 accidental burn wounds treated with various compositions.

Examples 2 thru 14 are all descriptions of accidental burns and scalds. No infectious complications were observed following application of any of the gel formulations, or liquid applications of vinegar or citric acid. While interpersonal variations are considerable, there was no doubt in the observers—one of whom is a physician—that the combination of 5% citric acid plus 1% vinegar or acetic acid was the most effective formulation with lasting effect, while citric acid gels were the least effective. Gel application rapidly after injury had the fastest, most impressive effects. These impressions were confirmed in 48 non-accidental burns (see FIG. 2 and Example 1) during an ongoing pre-clinical fact finding and pilot study involving adult volunteers. The results of these tests are summarized in FIG. 3.

Example 2

A white female (ID # 2) 46 years of age burned her dorsal hand with a bowl of hot soup. Within one minute of the trauma she immersed her hand in a bowl of vinegar (@ 5% acetic acid content). Pain was relieved within 20 seconds, pain reappeared gradually upon withdrawal from vinegar, and disappeared upon re-immersion. After about 5 minutes she removed hand from vinegar as the pain was gone, she resumed normal activity. No blisters and scars developed, she took a shower that evening and next morning without signs of hyperalgesia.

Example 3

A white waiter, 22 years of age (ID #22) was accidentally burned by a co-worker on his upper arm with a hot fajita frying pan. The burn was severe, 7 cm long and deep. Within less than 5 minutes, a clean, liberally vinegar soaked towel was applied to this wound, a second application was done 10 minutes later. Pain relief was achieved within less than 30 seconds of first application. Within 15 minutes post trauma, the waiter resumed normal work activity in the restaurant's lunch rush period. Two hours later the towel wrap, no dry, was removed and he was sent to a nearby walk-in clinic. There, a second degree, probably, was diagnosed, a sterile bandage and analgesics were offered, the latter declined by the patient. The lack of blistering was noted. An invitation for wound revisions over the next several days was declined. Wound healing proceeded without complications, there was no hyperalgesia and the wound was fully closed 4 weeks post trauma.

Example 4

A white female waitress, 21 years of age (ID # 24) scalded her entire dorsal hand area with fresh brewed coffee. Within 2 minutes we applied liquid vinegar followed by application of a liberally vinegar-soaked towel. Pain relief was complete within less than 30 seconds, and the person resumed her waiting duties unencumbered within 10 minutes of the accident. No blisters or scars developed.

Example 5

A white male waiter, 26 years of age (ID #25) burned his ventral thumb region with a hot fajita frying pan. Within 2 minutes, a linen towel was applied, liberally soaked with vinegar. Pain relief was complete within 20 seconds, the linen towel was removed within 10 minutes and normal work activities resumed. No blisters or scars developed.

Example 6

A white male, 50 years of age (ID # 42) accidentally burned the ventral hand region with a roasting pan, causing severe pain, local analgesics were applied with little relief. The trauma was immersed in a bowl of vinegar 40 minutes post trauma. Pain relief was complete within 1 minute, but it required 35–40 minutes before pain relief was stable and the victim could remove his hand from the bowl. Incipient blistering did not proceed, there was no hyperalgesia

Example 7

A black male cook, 31 years of age (ID #41) accidentally burned his dorsal hand region with boiling oil. Liquid vinegar was applied within 3 minutes. Pain relief was complete within 30 seconds. Vinegar gel (5%) was applied 2 minutes later, and pain relief was sustained. Normal work activity was resumed within 20 minutes post trauma. No blisters or scars developed. This victim had a very similar accident 5 months previously and was treated in a hospital emergency ward with several follow-up visits. He could not resume work until 12 days later.

Example 8

A white male waiter, 32 years of age (ID #39) accidentally burned the ventral region of 3 fingers on a hot plate. We applied Acetic Acid Gel (5%) within 5 minutes. Pain relief was complete within 30 seconds. Gel was reapplied 3 times over the next 10 minutes, normal work routine was resumed within 15 minutes. No blisters or scars developed.

Example 9

A white waitress, 48 years of age (ID # 44) accidentally scalded a large ventral forearm region with hot soup. We applied 5% Citric Acid Gel to the burn injury within 3 minutes. Pain relief was complete within 45 seconds. The gel was reapplied 3 times over the next 15 minutes. Normal work activity was resumed within 25 minutes. No blisters or scars developed.

Example 10

An Asian waitress, 35 years of age (ID #45) accidentally covered the dorsal hand region with boiling oil. We applied 5% Citric Acid & 1% Vinegar Gel within 4 minutes. Pain relief started immediately and was complete within less than 30 seconds. The gel was reapplied twice over the next 10 minutes and then removed. No pain redeveloped and normal work activity was resumed within 20 minutes. No blisters or scars evolved.

Example 11

A white waiter, 34 yeas of age (ID #46) was accidentally burned with a frying pan in the dorsal forearm region. We applied 5% Citric Acid & 1% Vinegar Gel within 1 minute. Pain relief was complete within 15 seconds. The gel was reapplied once and removed within 10 minutes, when normal work activity was resumed. No pain redeveloped. No blisters or scars evolved.

Example 12

A white male, 32 years of age (ID # 47) was accidentally burned with a frying pan on the ventral forearm. 5% Citric Acid & 1% Vinegar Gel was applied within 5 minutes. Pain relief began immediately and was complete within 20 seconds. The gel was reapplied twice over the next 15 minutes and then removed. No pain redeveloped. No blisters or scars evolved.

Example 13

A white waitress, 29 years of age (ID #48) was accidentally burned with a frying pan on the ventral forearm. We applied 5% Citric Acid & 1% Vinegar Gel within 1 minute. Pain relief was complete within 15 seconds. The gel was reapplied once and removed 10 minutes post trauma. No pain redeveloped and normal work activity resumed. No blisters or scars evolved.

Example 14

A white male, 46 years of age (ID #6) was burned with a glue gun on the dorsal forearm. We applied neutral 'Water Gel' within one minute. There was no pain relief, but the gel seemed to cool the injury somewhat. By 2 hours post trauma 5% Citric Acid & 1% Vinegar Gel became available and was applied. Pain relief was complete within 20 minutes. A blister had developed by this time, but blister formation did not proceed and actually receded over the next following hours. The 5% Citric Acid & 1% Vinegar Gel was reapplied 4 times within that period. The wound is presently healing without complications.

Example 15

Series of Controlled Burn Tests on Human Volunteers Controlled, physician-observed tests on human, adult volunteers: a localized, 2.5 cm2 thermotrauma was produced on the -lateral forearm through 5–7" contact with a heated (300° C.) metallic probe. This produces a 2nd degree burn trauma with blistering and intense pain. Untreated it will develop into a second degree exacerbated (category-IIb-type) trauma in 50–60% of applications. Up to four, but usually 2 burn traumas were applied per subject and occasion. The primary test endpoint was pain relief, the secondary endpoint was presence/absence of blistering, the tertiary endpoint was presence absence of hyperalgesia (undue pain) following exposure to warm water (at a temperature chosen by the subject for normal shower) 12–14 hours after the test insult. Test subjects were physician observed for 1 hr post trauma and several times (4–8 times) over a 2–4 week period thereafter.

For ethical reasons, the effective formula was provided to all volunteers by the end of this period, usually after 60 minutes. Several different formulations were tested successively and repeatedly on the same burn, to provide comparative data. These tests were only occasionally blinded. In the 48 patients (see FIG. 2) of these non-accidental burns provided, only results of the initial treatment is indicated. Acceleration of wound healing was not an endpoint of this study, but the very rapid re-gain of function and absence of 1.) a single secondary infection, 2.) a single incident of posttraumatic wound exacerbation was a uniform finding.

Example 16

Critical experiment was performed on human volunteers. forearm skin area was overlaid with either acetic acid/citric acid- or water gel for 45 seconds and the gel then removed with a dry cotton swab. The standard heat trauma was then applied to the same areas. There was protection from pain in the area previously overlaid with acetic acid/citric acid gel, but not the water (neutral) gel, where pain relief was rapid following application of a composition of the instant invention. While pain relief was consistently observed in the traumata pre-treated with the acetic/citric acid gel formulation of the instant invention, there was limited, but definitive blistering, and no accelerated healing in several tests.

The present invention provides an attractive, affordable, chemically stable and easily transportable choice for the majority of burn accidents.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification and drawings.

What is claimed is:

1. A method for treating burns comprising applying to the affected area of the skin a composition comprising a therapeutically effective amount of one or more weak organic acids selected from the group consisting of acetic acid, vinegar, citric acid and combinations thereof, in a pharmacologically effective carrier including about 0.1% EDTA, wherein the pH of the composition ranges from approximately 2.5 to 4.5;
   wherein said therapeutically effective amount provides treatment of delayed hyperalgesia.

2. A method according to claim 1 wherein the pH ranges from 4.1 to 4.4.

3. A method according to claim 2 wherein the pH ranges from 4.15 to 4.25.

4. A method according to claim 3 wherein the pH is approximately 4.2.

5. A method according to claim 1 wherein the carrier includes a gelling agent.

6. A method according to claim 5 wherein the gelling agent is a cross-linked acrylic acid-based polymer.

7. A method according to claim 1 further including one or more agents selected from the group consisting of sunblocking agents, skin moisturizing agents, herb extracts and antimicrobial agents.

8. A method according to claim 6 wherein the composition includes an effective amount of a Marigold extract, an aloe vera extract or a combination thereof.

9. A process for mediating the perception of pain in an area of tissue damaged by excessive exposure to thermal, frictional, chemical, electrical, radiation and/or radioactive agents comprising:
   exposing said area of tissue damage to a prolonged and localized concentration of H+ ions; and
   maintaining said concentration of H+ ions in contact with said area of tissue damage for a time sufficient to alleviate any perception of pain;
   wherein said H+ ions are provided by a composition containing a therapeutically effective amount of one or more weak organic acids selected from the group consisting of acetic acid, vinegar, citric acid and combinations thereof, dispersed within a pharmacologically effective carrier including about 0.1% EDTA, wherein the pH of the composition is within the range of approximately 2.5 to 4.5, and wherein said therapeutically effective amount provides treatment of delayed hyperalgesia.

10. A process in accordance with claim 9, wherein the source of H+ ions is a composition containing a combination of either acetic acid or vinegar in an amount to yield up to about 0.5 to 5% acetic acid and about 2 to 8% citric acid.

11. A process in accordance with claim 10, wherein the composition comprises a combination of either acetic acid or vinegar in an amount to yield up to about 1% acetic acid and about 5% citric acid.

12. A process according to claim 9, wherein the pH ranges from 4.1 to 4.4.

13. A process according to claim 12, wherein the pH ranges from 4.15 to 4.25.

14. A process according to claim 13, wherein the pH is approximately 4.2.

15. A process according to claim 9, wherein the carrier includes gelling agents.

16. A process according to claim 15 wherein the gelling agent is a cross-linked acrylic acid-base polymer.

17. A process according to claim 15, further including one or more agents selected from the group consisting of sunblocking agents, skin moisturizing agents, herb extracts and antimicrobial agents.

18. A method in accordance with claim 1, wherein said therapeutically effective amount further provides prophylaxis of wound infection.

19. A method in accordance with claim 1 wherein
   said therapeutically effective amount further provides local analgesia.

20. A method in accordance with claim 1, wherein said therapeutically effective amount further provides treatment or reduction of hyperemia.

21. A method in accordance with claim 1, wherein said therapeutically effective amount further provides treatment or reduction of local edema.

22. A method in accordance with claim 1, wherein said therapeutically effective amount further provides treatment of blister formation.

23. A method in accordance with claim 1, wherein said therapeutically effective amount further provides unimpeded wound healing.

24. A method in accordance with claim 1, wherein said therapeutically effective amount further provides treatment of depigmentation.

25. A method in accordance with claim 1, wherein said therapeutically effective amount further provides absence of scarring and keloid formation.

* * * * *